(12) United States Patent
Prive (10) Patent No.: US 7,087,729 B1
(45) Date of Patent: Aug. 8, 2006

(54) PEPTIDE CONJUGATES FOR THE STABILIZATION OF MEMBRANE PROTEINS AND INTERACTIONS WITH BIOLOGICAL MEMBRANES

(75) Inventor: Gil Prive, Toronto (CA)

(73) Assignee: University Health Network, Toronto (CA)

( * ) Notice: Subject to any disclaimer, the term of this patent is extended or adjusted under 35 U.S.C. 154(b) by 201 days.

(21) Appl. No.: 10/019,482

(22) PCT Filed: Jun. 29, 2000

(86) PCT No.: PCT/CA00/00773

§ 371 (c)(1),
(2), (4) Date: Jun. 18, 2002

(87) PCT Pub. No.: WO01/02425

PCT Pub. Date: Jan. 11, 2001

Related U.S. Application Data (60) Provisional application No. 60/140,986, filed on Jun. 29, 1999.

(51) Int. Cl.
*A61K 38/00* (2006.01)

(52) U.S. Cl. .................................... 530/402
(58) Field of Classification Search ................ 530/402
See application file for complete search history.

(56) References Cited

FOREIGN PATENT DOCUMENTS

WO          99/55383          11/1999

OTHER PUBLICATIONS

Online-Medical Dictionary. "Amino acid". http://cancerweb.ncl.ac.uk/cgi-bin/omd?query=amino+acid. Nov. 13, 1997.*
P. Berndt, et al., "Synthetic lipidation of peptides and amino acids: monolayer structure and properties" Journal of the American Chemical Society, vol. 117, No. 37, 1995, pp. 9515-9522.
Christian E. Schafmeister, et al., "Structure at 2.5 A of a Designed Peptide that Maintains Solubility of Membrane Proteins" Science, vol. 262, Oct. 29, 1993.

* cited by examiner

*Primary Examiner*—Christopher R. Tate
*Assistant Examiner*—Maury Audet
(74) *Attorney, Agent, or Firm*—Crowell & Moring LLP (57) ABSTRACT

The present invention provides a novel class of detergents referred to herein as lipopeptide detergents. Lipopeptide detergents comprise an amphipathic α-helical peptide having a hydrophobic or neutral face and a hydrophilic face. To each end of this peptide is covalently linked an aliphatic hydrocarbon tail, these aliphatic tails being linked thereto such that they associate with the hydrophobic or neutral face of the peptide. Lipopeptide detergents can advantageously be used to stabilize membrane proteins in the absence of a phospholipid bilayer in a manner that preserves the native conformation and permits the subsequent crystallization thereof.

17 Claims, 6 Drawing Sheets

PEPTIDE CONJUGATES FOR THE STABILIZATION OF MEMBRANE PROTEINS AND INTERACTIONS WITH BIOLOGICAL MEMBRANES

This application claims the benefit of U.S. Provisional Application No. 60/140,988, filed Jun. 29, 1999.

FIELD OF THE INVENTION

This invention generally relates to compounds that have utility as detergents. In particular, the present invention relates to a novel class of peptide-based chemical compounds that interact with proteins, lipids and other molecules. The compounds may be used for the stabilization and crystallization of proteins and membrane proteins, in particular. The compounds are also useful for modifying the properties of lipid bilayer membranes, and have potential uses as cytolytic agents, as molecules that can facilitate the transport of polar molecules across biological membranes, and as emulsifiers and surfactants.

BACKGROUND OF THE INVENTION

Membrane proteins are critical components of all biological membranes, and can function as enzymes, receptors, channels and pumps. They are also very common in biological systems, as 20–40% of the genes found in the bacteria, archaea and eukaryotes code for membrane proteins (Wallin and von Heijne, *Protein Sci,* 7, 1029–38 (1998), Boyd, et al., *Protein Sci,* 7, 201–5 (1998), Gerstein, *Proteins,* 33, 518–34 (1998), Jones, *FEBS Lett,* 423, 281–5 (1998), Arkin, et al., *Proteins,* 28, 465–6 (1997)). Many clinically useful drugs, including the widely prescribed drugs, fluoxetine (Prozac™) and omeprazole (Prilosec™), interact with human membrane proteins. However, despite the abundance and importance of membrane proteins, this class of molecules is still only poorly understood at a structural level, mainly because of difficulties in growing crystals of membrane proteins suitable for analysis by x-ray crystallography (Garavito, et al., *J Bioenerg Biomembr,* 28, 13–27 (1996), Ostermeier and Michel, *Curr Opin Struct Biol,* 7, 697–701 (1997), Garavito, Curr Opin Biotechnol 9, 344–349 (1998)).

In order to understand the mechanism of action of a particular membrane protein, it is essential to know the three-dimensional structure of the molecule to a resolution that reveals its atomic structure. This is typically taken to be better than 0.3 nm resolution, and nearly all of the membrane protein structures that are known to this resolution have been determined by the technique of x-ray crystallography (Branden and Tooze, *Introduction to Protein Structure,* Garland Publishing Inc., New York (1998)). If the protein in question is medically important, knowledge of the 3-dimensional structure of the protein is a prerequisite for the development of new therapeutics using structure-based rational drug design methodologies (for example, see Klabunde, et al., *Nature Structural Biology* 7, 312–321 (2000)). The techniques used in the study of membrane protein crystals are very similar to those used for crystals of soluble proteins, and the main barrier to advancement in this field is the generation of diffraction-quality crystals.

The techniques used for the crystallization of membrane proteins are generally similar to the techniques used for the crystallization of soluble proteins, and include vapour diffusion, microdialysis and batch methods (A. McPherson, in "Crystallization of Biological Macromolecules", Cold Spring Harbour Press (1998)). Typically, a purified, concentrated solution of protein is brought to the limit of its solubility over the course of days or weeks, resulting in either the formation of a protein precipitate or of protein crystals. Because precipitates are more often observed than crystals, numerous conditions are tested in these trials. The number of trials can vary in number from a few dozen to several thousand in attempts to find conditions resulting in crystal formation. The tested conditions can differ in pH, nature of added salts, concentration of the added salts, nature of the precipitant, concentration of the precipitant, temperature, and other factors (A. McPherson, in "Crystallization of Biological Macromolecules", Cold Spring Harbour Press (1998)). In some instances, conditions producing suitable crystals for analysis by x-ray diffraction are not discovered even after extensive screening.

If the protein under consideration is an intrinsic membrane protein, the protein sample used in the crystallization trials is first purified and stabilized in a specific detergent in order to preserve the native conformation of the protein in the absence of a lipid bilayer (H. Michel, *Trends Biochem. Sci.* 8, 56–59 (1983), W. Kuhlbrandt, *Quart. Rev. Biophysics* 21, 429–477 (1988)). In most instances, a number of different detergents are tested for their ability to stabilize a particular membrane protein, and for their effect in the crystallization trials. Examples of detergents suitable for these purposes include the alkyl gylcoside detergents such as octyl β-D-glucopyranoside (OG, octyl glucoside) and dodecyl β-D-maltopyranoside (DDM, dodecyl maltoside) (Baron and Thompson, *Biochim. Biophys. Acta* 382, 276–285 (1975), Rosevear et al., *Biochemistry* 19, 4108–4115 (1980)), the polyoxyethylene alkyl ether detergents such as pentaethylene glycol monooctyl ether (C8E5) and octoethylene glycol monododecyl ether (C12E8) (Garavito and Rosenbusch, Meth. Enzymol. 125, 309–328 (1886), Victoria and Mahan, Biochim Biophys Acta 644, 226–232 (1981)), and the detergents described in U.S. Pat. No. 5,674,987, which are prepared from the reaction of a cycloalkyl aliphatic alcohol and a saccharide. Detergent-solubilized membrane proteins exist as protein-detergent complexes (PDC) in which a cluster of detergent molecules covers the surface of the protein that is normally exposed to the lipophilic core of the lipid bilayer. The hydrophobic portions of the detergent amphiphiles interact with the protein surfaces normally in contact with the lipid acyl chains, and thus mimic the normal lipid environment at the surface of the membrane protein. This micelle-like ring of detergent molecules surrounding the membrane protein is very dynamic and mobile, such that the surface properties of the PDC is in general poorly suited to the formation of well-ordered crystals (Crystallization of Membrane Proteins, H. Michel ed. CRC Press, Boca Raton, Fla. (1991)). This unfavorable effect is lessened in cases where the protein has large extramembranous domains, or with detergents that have small micellar volumes.

A number of techniques have been developed to address this difficulty in attempts to achieve membrane protein crystallization. For example, the formation of a complex with an antibody fragment has been used to increase the polar surface area of the *Paracoccus denitrificans* cytochrome oxidase, resulting in well-diffracting crystals (Ostermeier et al., Nat Struct Biol, 2, 842–6 (1995), Ostermeier et al., Proc Natl Acad Sci USA, 94, 10547–53 (1997)). Fusion proteins of the membrane protein lactose permease with soluble carrier domains have been made in attempts to achieve a similar result (Privé et al., Acta Cryst D50, 375–379 (1994), Privé and Kaback, J Bioenerg Biomembr 28, 29–34 (1996)). Bacteriorhodopsin (BR) has been crystallized from cubic lipid phases (Landau and Rosenbusch, Proc Natl Acad Sci USA, 93, 14532–5 (1996)) in a method that does not rely on detergents at all. However, few crystals suitable for structure determination have been produced by this method (Chiu, et al., *Acta Crystallogr D*56, 781–784 (2000)). A strategy to reduce the volume and dynamics of the detergent surface of the PDC has been proposed by Schafineister et al. (Science, 262, 734–8 (1993)). In this approach, amphipathic peptides have been used in the place of traditional detergents such as octyl glucoside. The peptides were designed such that the peptide would form an α-helix with one hydrophilic face and one hydrophobic face. The intention was that the hydrophobic surface was of the peptide would associate with the transmembrane surface of a membrane protein. Although the peptide used in this study could maintain some membrane proteins in a solubilized state for a few days, the proteins were not sufficiently stabilized for the purposes of crystallization. Because of their limited effectiveness as detergents, these peptides have not found general utility as tools for the study of membane proteins.

In the traditional detergents consisting of a polar head group and a linear alkyl tail, the length of the hydrocarbon moiety is an important factor in determining the ability of the detergent to preserve the native conformation of a solubilized membrane protein. Within the framework of a common head group, longer chain length detergents are generally more stabilizing towards membrane proteins, and are considered to be more "gentle". The presumed mechanism for stabilization is that the longer chains are deemed to be more effective at masking the hydrophobic transmembrane surface of the membrane protein than the short chain detergents and are thus better mimics of the native membrane environment. However, longer chain detergents occupy a larger volume of the belt region of the PDC, a feature that is expected to reduce the probability of crystallization of the complex (Michel, 73–87 in "Crystallization of Membrane Proteins", H. Michel, ed., CRC Press. Boca Raton, Fla. (1991)). Another factor affecting the choice of a particular detergent is the solubility of the detergent in water or buffer solutions. As the alkyl chain length increases in a series of detergents with a common head group, the overall solubility of the detergent decreases, eventually to levels making the detergent impractical for most uses. Thus, octyl glucoside is soluble to levels greater than 20% (w/v) in water, while decyl glucoside is soluble to only 0.1% (w/v) in similar conditions, and dodecyl glucoside is soluble only to 0.008% (w/v) (Anatrace Inc., Maumee Ohio 1999–2000 Catalogue). With a larger head group such as maltoside, the solubility of the long chain detergents increases, but solubility is still reduced to impractical levels with hexadecyl chain lengths or longer. Thus, within a series of traditional detergents, there is conflct in the preferred length of the alkyl chain length. Long chains favor protein stability, and short chains are optimal for crystallization and detergent solubility. Since protein stability is a prime concern for crystallization trials, many membrane protein crystallization trials are carried out under sub-optimal conditions.

Thus, a major use of non-denaturing detergents is for the preservation of the biological function of a membrane protein in the absence of a lipid bilayer. These conditions are often encountered during the handling of membrane proteins, and in particular during the purification of membrane proteins, and during crystallization trials.

There is a need, thus, for a non-denaturing detergent which effectively mimics the membrane's lipid bilayer, is capable of solubilizing membrane proteins in such a way that the three-dimensional conformation is retained, and has features to enhance the probablility of crystallization of membrane proteins.

SUMMARY OF THE INVENTION

Accordingly, in one aspect, the present invention provides an amphipathic peptide conjugate having detergent properties and having a hydrophobic face and a hydrophilic face, said peptide moiety of the conjugate comprising a first end and a second end, wherein said first end is covalently linked to a first aliphatic hydrocarbon moiety and said second end is covalently linked to a second aliphatic hydrocarbon moiety, said aliphatic moieties being linked such that they associate with the peptide moiety of the conjugate.

Preferably the peptide conjugate is a lipopeptide detergent.

Generally, a purified protein in a known detergent is subjected to a process whereby the known detergent is exchanged for the novel detergent of the present invention. The protein in the novel detergent may then be subjected to conditions that promote crystallization to occur.

BRIEF DESCRIPTION OF THE DRAWINGS

The present invention is described in further detail herein by reference to the following drawings in which.

DETAILED DESCRIPTION OF THE INVENTION

Detailed Description of the Drawings

FIG. 1 is a schematic representation of the lipopeptide detergents. FIG. 1A shows a single LPD molecule with the α-helical peptide represented in a Cα tracing with grey lines, and the aliphatic acyl chains of two fatty acids coupled to side chains at either end of the peptide shown with black lines. This representation is the presumed conformation of the monomer within the assembly shown in FIG. 1B. FIG. 1B shows the presumed assembly of the peptides into a cylindrical assembly. The fatty acyl chains cluster in the core of the assembly, near the central axis of the cylinder. FIG. 1C shows a schematic representation of a membrane protein solubilized by a traditional detergent. This is included to show the contrast between the present invention and the prior art. FIG. 1D shows a similar protein solubilized by a lipopeptide detergent.

Figure 2A:
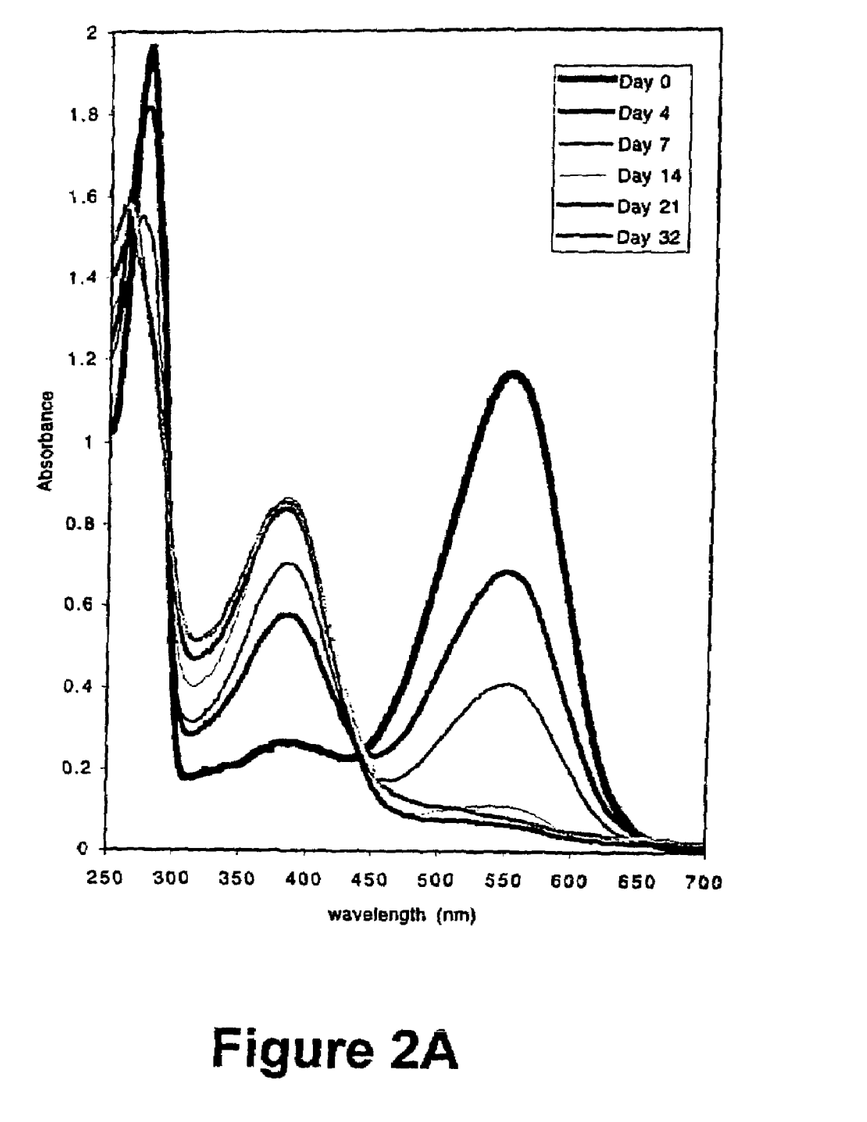
FIG. 2A is a graph of a series of absorption spectra of the membrane protein bacteriorhodopsin in the traditional detergent octyl glucoside (OG) showing the loss of the native conformation of the protein over time.
Figure 2B:
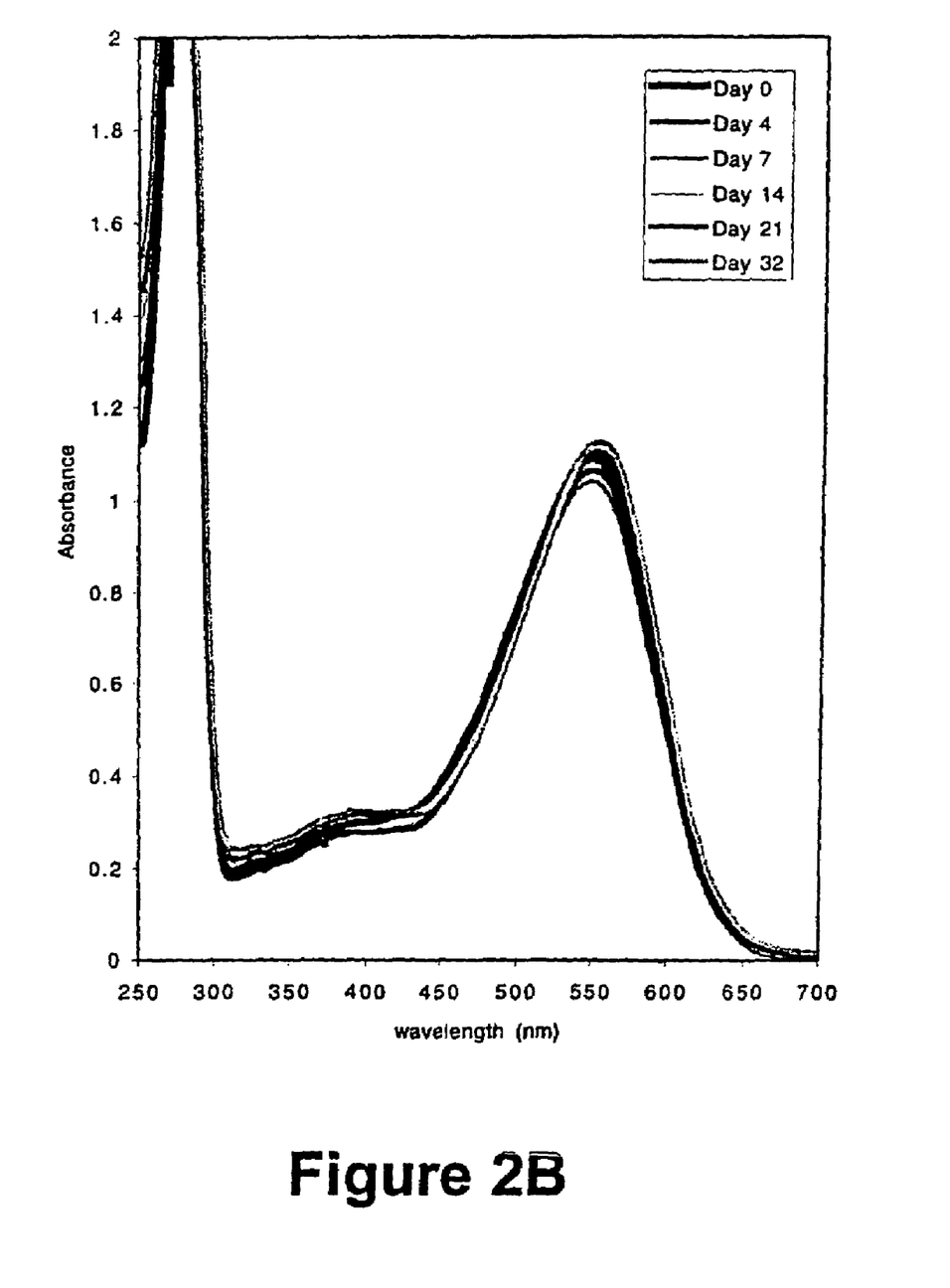
FIG. 2B is a graph of a series of absorption spectra of the membrane protein bacteriorhodopsin in the lipopeptide detergent LPD-16 showing the preservation of the native conformation of the protein over the course of 32 days.
Figure 2C:
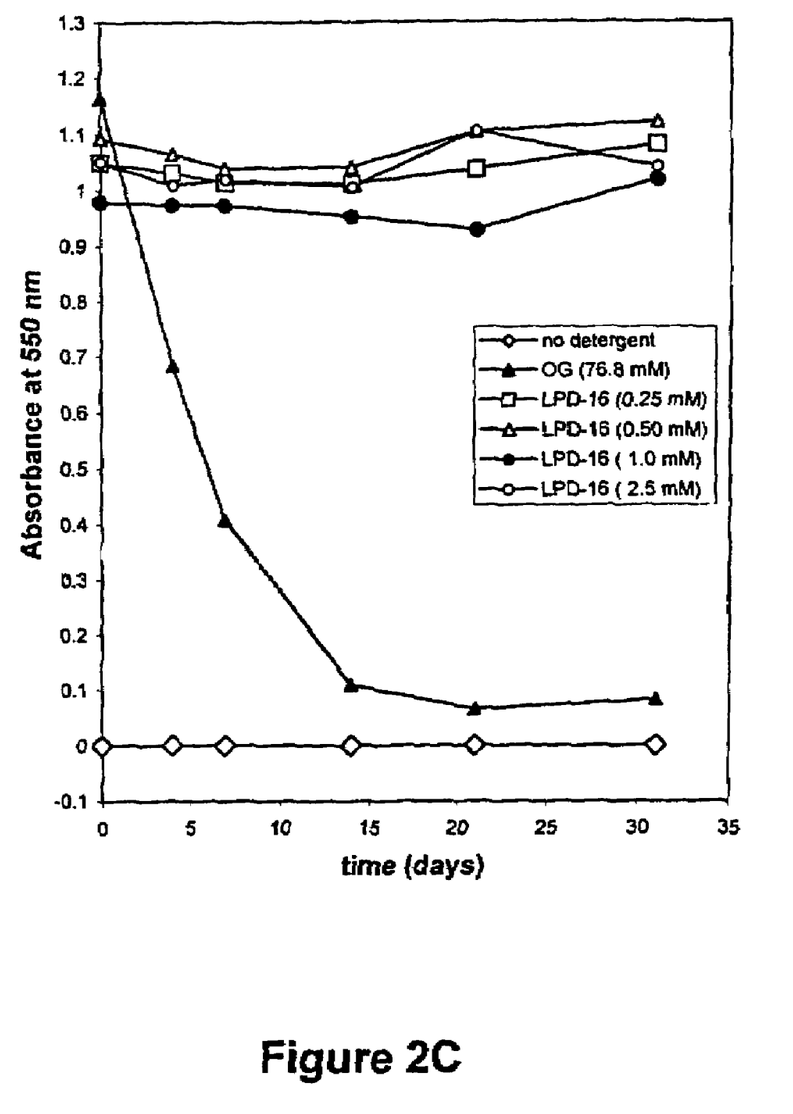
FIG. 2C is a graph showing the effectiveness of different concentrations of the lipopeptide detergent LPD-16 in maintaining the membrane protein bacteriorhodopsin in a soluble, stable state in the absence of a phospholipid membrane.
Figure 2D:
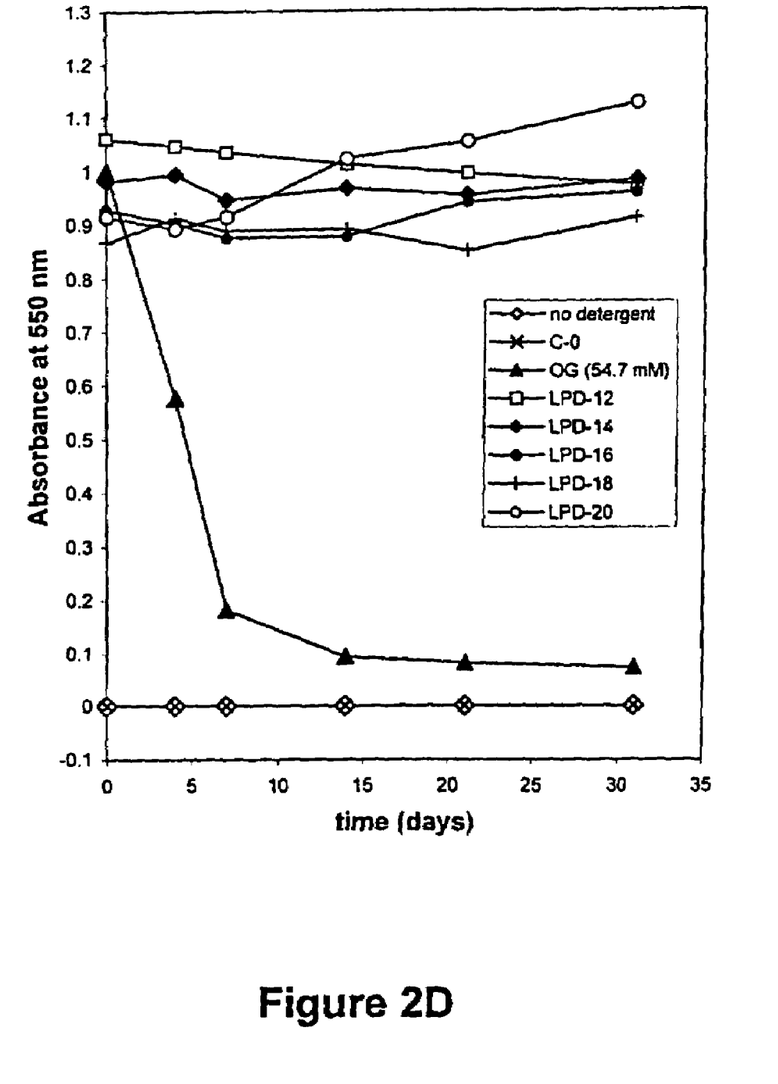
FIG. 2D is a graph showing the effectiveness of 5 lipopeptide detergents (LPD-12, LPD-14, LPD-16, LPD-18, LPD-20) in maintaining the membrane protein bacteriorhodopsin in a soluble, stable state in the absence of a phospholipid membrane.
Figure 3:
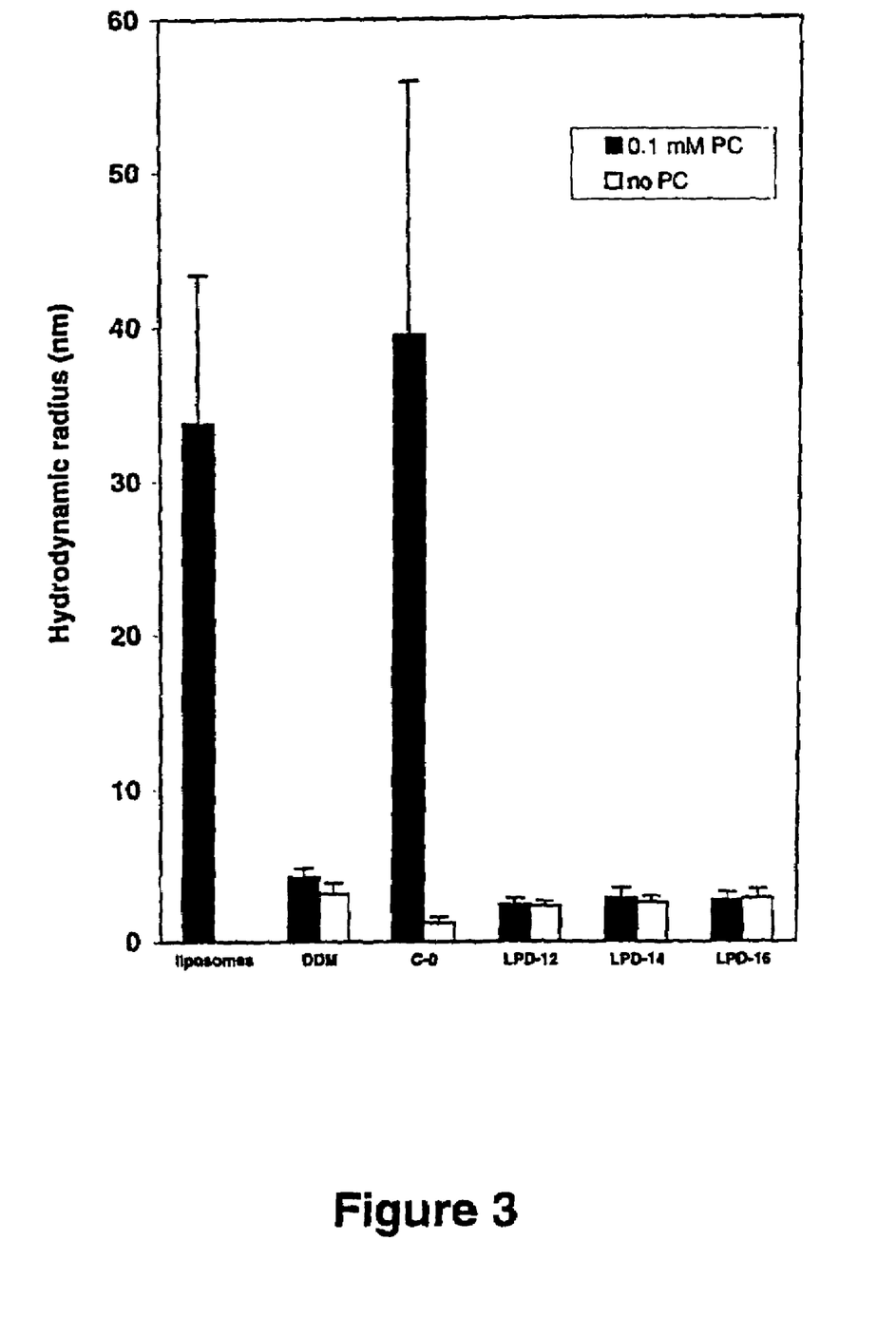
FIG. 3 is a histogram demonstrating that the lipopeptide detergents LPD-12, LPD-14 and LPD-16 interact with phospholipid membranes, dissolving them into micelles.

FIGS. 2 and 3 are discussed in detail later in the description.

The present invention provides novel lipopeptide detergents comprising an α-helical peptide scaffold having aliphatic hydrocarbon tails covalently linked to opposite ends of the peptide scaffold.

The peptide scaffold is not particularly limited with respect to its amino acid sequence.

Figure 1A:
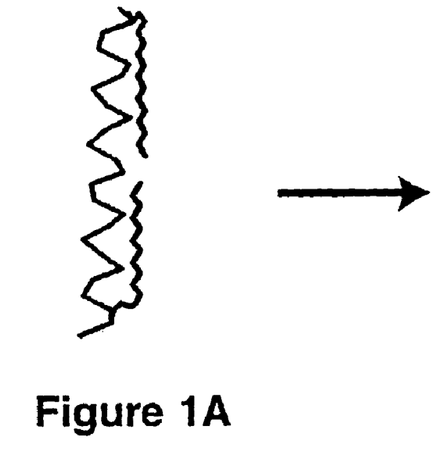
FIG. 1A is a schematic representation of a single lipopeptide detergent (LPD) molecule in accordance with the present invention.
Figure 1B:
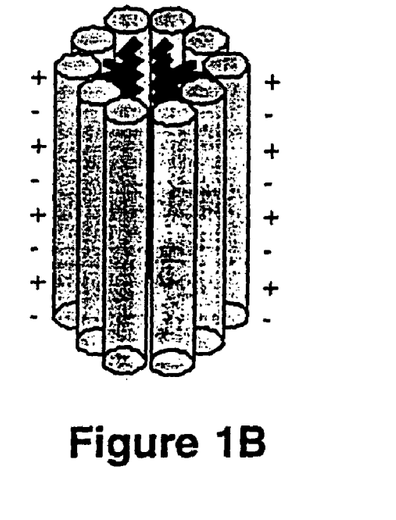
FIG. 1B is a schematic representation of a cylindrical assembly of several lipopeptides in which the aliphatic hydrocarbon tails are clustered in the core of the assembly.
Figure 1C:
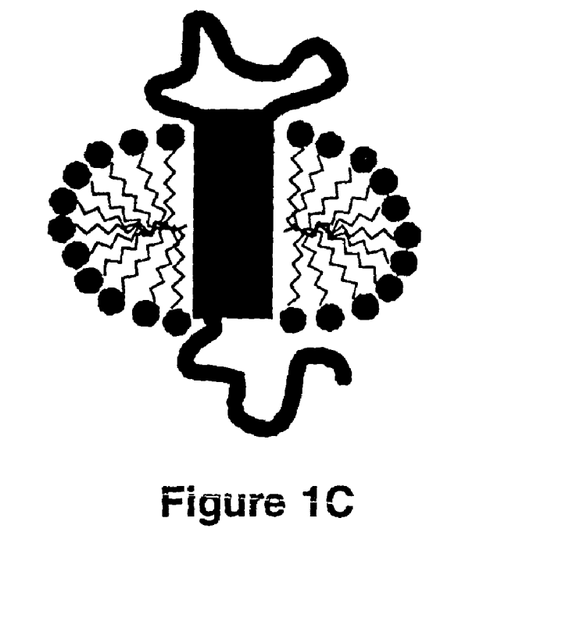
FIG. 1C is a schematic representation of a membrane protein solubilized by a traditional detergent (prior art)

However, the amino acid sequence is selected so as to permit formation of the peptide scaffold into an amphipathic α-helical conformation. Generally, the peptide will comprise a mixture of hydrophobic and hydrophilic regions. Hydrophobic regions will include, but are not limited to, neutral or hydrophobic amino acids such as alanine, valine, leucine, isoleucine, methionine, phenylalanine, tryptophane or amino acids that do not occur in nature. Preferably, the hydrophobic regions are alanine-rich to favor the formation of an α-helical conformation (Chakrabartty et al., *Protein Sci*, 3, 843–52 (1994). The hydrophilic regions will include, but are not limited to, amino acids, which are primarily hydrophilic in nature such as glutamate, lysine, glutamine, aspartate, asparaginine, histidine, serine, tyrosine, threonine or amino acids that do not occur in nature. Preferably, the hydrophilic regions promote helix formation through the formation of (i,i+4) salt bridges (Marqusee and Baldwin, *Proc Natl Acad Sci USA*, 84, 8898–902 (1987)). The hydrophilic regions of the peptide align on the face of the helix that will interact with bulk aqueous phase when in a lipopeptide assembly as shown in FIG. 1B. The neutral or hydrophobic face will include two residues for covalent coupling of the aliphatic moieties in the peptide conjugate. These residues will be near the termini of the peptide, at positions where they are aligned with the hydrophobic face of the peptide. The two residues can be lysine, ornithine, cysteine, glutamate or aspartate residues, but are not limited to these amino acids. Preferably, the two residues are ornithines.

The number of amino acids in the peptide scaffold is variable, and will generally be selected such that the length of the peptide scaffold when in an α-helical conformation will approximate the width of a natural membrane phospholipid bilayer, i.e. between 3.0–4.5 nm. Accordingly, the number of amino acids in the peptide scaffold will range from about 15 to 35 amino acids. Preferably, the number of amino acids in the scaffold will be about 20–30. More preferably, the peptide scaffold will include about 25 amino acids, or a number of amino acids which when in an α-helical conformation measure a length of about 3.7 nm.

The terminal amino acids of the peptide scaffold are also selected to promote α-helix formation, and may be naturally occurring amino acids or modified forms thereof.

Modifications commonly made to terminal amino acids in peptides include the addition of groups conventionally used in the art of peptide chemistry, which will not adversely affect the function of the lipopeptide. For example, suitable N-terminal blocking groups can be introduced by alkylation or acylation of the N-terminus. Examples of suitable N-terminal blocking groups include $C_1$–$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal residue. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide function. Preferred examples of such modifications include N-terminal acetylation and C-terminal amidation which are known to promote α-helix formation (Doig et al., *Biochemistry*, 33, 3396–403 (1994)).

Internal amino acids of the peptide may also be modified by derivatization provided that this modification does not affect the function of the lipopeptide, and does not interfere with its α-helical conformation. Such derivatizations can be made to the side chains of the amino acids. For example, the side chains can derivatized by incorporation of blocking groups as described above.

The peptide conjugate may be readily prepared by standard, well-established solid-phase peptide synthesis (SPPS) as described by Stewart et al. in *Solid Phase Peptide Synthesis*, 2nd Edition, 1984, Pierce Chemical Company, Rockford, Ill.; and as described by Bodanszky and Bodanszky in *The Practice of Peptide Synthesis*, 1984, Springer-Verlag, New York, and as described in Novabiochem Catalogue and Peptide synthesis handbook, 1997–1998. Other synthetic protocols, including biological or solution phase methods, can also be used. For the SPPS method, a suitably protected amino acid residue is first attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions, which will not affect the final peptide product. Stepwise synthesis of the oligopeptide is carried out by the removal of the N-protecting group from the initial amino acid, and coupling thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenylesters.

Examples of solid phase peptide synthesis methods include the Boc method which utilizes tert-butyloxycarbonyl as the α-amino protecting group, and the Fmoc method which utilizes 9-fluorenylmethyloxycarbonyl to protect the α-amino of the amino acid residues, both methods of which are well-known by those of skill in the art.

The aliphatic moieties can be coupled to the resin-coupled peptide by selectively deblocking amino acid side chain protecting groups, followed by reaction with an appropriate aliphatic derivative. Aliphatic derivatives suitable for this purpose include, but are not limited to, saturated fatty acids, unsaturated fatty acids, branched fatty acids, cyclic alkyl acids, aromatic alkyl acids, alkyl amines, alkyl maleimides, alkyl acid chlorides, and alkyl anhydrides. Several strategies can be used to couple the aliphatic derivative to the peptide. For example, if the peptide is synthesized with the Fmoc method, a Boc group can be used as the protecting group on the δ-amino group of the ornithine monomers identified as sites for aliphatic coupling. Upon completion of the synthesis of the main peptide chain, the ornithine Boc groups can be selectively removed with trifluoroacetic acid, generating free primary amino functionalities at these positions. Reaction with an aliphatic derivative such as a fatty acid can be used to form an amide linkage with each of the two ornithine side chains. Examples of suitable saturated fatty acids include octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nondecanoic acid, eicosanoic acid, heneicosaoic acid, docosanoic acid, tricosanoic acid, tetracosanoic acid, pentacosanoic acid, hexacosanoic acid, heptacosanoic acid and octacosanoic acid. Following the coupling of the aliphatic groups, the remaining amino acid side chains can be deblocked under appropriate conditions, such as with hydrofluoric acid (HF) or trifluoromethanesulfonic acid (TFMSA).

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with HF or TFMSA releases the desired C-terminally amidated peptide. Similarly, incorporation of an N-methylamine blocking group at the C-terminus is achieved using N-methylaminoethyl-derivatized divinyl benzene (DVB) resin, which upon treatment with HF releases a peptide bearing an N-methylamidated C-terminus. Blockage of the C-terminus by esterification can also be achieved using conventional procedures. This entails use of resin/blocking group combination that permits release of sidechain protected peptide from the resin, to allow for subsequent reaction with the desired alcohol, to form the ester function. Fmoc protecting groups, in combination with DVB resin derivatized with methoxyalkoxybenzyl alcohol or equivalent linker, can be used for this purpose, with cleavage from the support being effected by trifluoroacetic acid (TFA) in dicholoromethane (DCM). Esterification of the suitably activated carboxyl function e.g. with N-N'-dicyclohexylcarbodiamide (DCC), can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry (MS) to determine the molecular weight of the peptide. Alternatively, or additionally, the amino acid content of the peptide can be confirmed by hydrolyzing the peptide in aqueous acid, and separating, identifying and quantifying the components of the mixture using reversed-phase high-pressure liquid chromatography (HPLC), or an amino acid analyzer. Protein sequenators, which sequentially degrade the peptide and identify the amino acids in order, may also be used to determine definitely the sequence of the peptide.

Having obtained the desired peptide conjugate, purification to remove contaminants is generally then conducted. Any one of a number of conventional purification procedures may be used to attain the required level of purity including, for example, ion-exchange and gel filtration chromatography or reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid or hydrochloric acid. Because the overall hydrophobicity of the peptide conjugates increases with larger aliphatic moieties, $C_4$-silica is the preferred chromatographic resin for these compounds.

Aliphatic hydrocarbon moieties are linked in a covalent manner to both the N- and C-termini of the scaffold peptide or to sites near each of these termini such that they associate with the hydrophobic region of the peptide scaffold. In one embodiment of the present invention, the aliphatic hydrocarbon tails are linked to ornithine residues located adjacent to N- and C-terminal alanine residues of the scaffold peptide. The δ-amino groups of the ornithines are coupled to the carboxyl groups of hexadecanoic acid via amide linkages. Ornithines are used in place of the more common lysine residues as sites for the hydrocarbon tail linkage since they have fewer methylene groups between the main chain peptide atoms and the side chain amine, and may position the hydrocarbon chains more precisely in association with the hydrophobic region of the peptide. Other types of covalent linkages between the peptide scaffold and the aliphatic hydrocarbon moiety are possible, and can include, but are not limited to, disulfide or ester linkages.

Figure 1D:
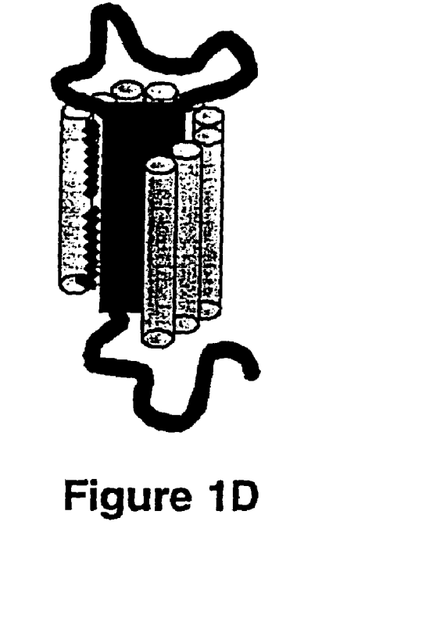
FIG. 1D is a schematic representation of a membrane protein solubilized by a lipopeptide detergent in accordance with the present invention.

The lipopeptide detergent is advantageous over "traditional" detergents such as OG due to its presumed ability to self-associate into a cylinder of defined dimensions. The cylinders are made up of colinear α-helices and themselves associate into a cylindrical assembly, as shown in FIG. 1B, in which the hydrophilic surfaces of the individual helices are exposed to the bulk aqueous phase and the hydrocarbon tails are packed in the core of the assembly effectively mimicking the chains in a membrane phospholipid bilayer. FIG. 1D illustrates how a membrane protein can be accommodated in the core of a lipopeptide assembly with the aliphatic hydrocarbon tails forming a cylindrical layer against the protein, again better mimicking biological membrane conformation, allowing for preservation of the biological activity of solubilized membrane proteins.

The described lipopeptide detergents with two coupled aliphatic moieties ranging from ten to twentyfour carbon alkyl chains are soluble in water, in contrast to an alkyl chain length maximum of sixteen carbon groups in the traditional detergents. The favorable solubility properties of the long chain lipopeptide detergents make it possible for these detergents to stabilize large hydrophobic surfaces of membrane proteins.

In addition to their stabilizing properties, the present lipopeptide detergents have been designed to favor the crystallization of membrane proteins. They lie close to the surface of the membrane protein, and are thus less obtrusive to the formation of a crystal lattice. Also, they present a rigid outer surface of α-helices. These are features that favor membrane protein crystallization (Schafineister et al., *Science*, 262. 734–8 (1993) Michel, in *Crystallization of membrane proteins*, 73–87 (1991)).

The lipopeptide detergents of the present invention may be used to crystallize membrane proteins. Generally, the method comprises solubilizing the membrane protein with a detergent, and then exposing the solubilized membrane to conditions which promote crystallization to occur.

The lipopeptide detergents are also membrane-active compounds, and can insert into phospholipid bilayers. At sufficiently high concentrations, they can disrupt the bilayers and form mixed lipid/lipopeptide micelles.

The lipopeptide detergents of the present invention have the activities of traditional detergents and hence they may be used to modulate and disrupt biological membranes, and therefore to transport polar molecules across membranes, including ions. As surface active agents or emulsifiers, they may be used in protein and/or lipid emulsions. They may also be used as cytolytic agents.

EXAMPLES

Embodiments of the present invention are described in further detail by reference to the following specific examples, which are not to be construed as limiting the appended claims.

Example 1

Synthesis of LPD-16

The lipopeptide, LPD-16, exemplifies a lipopeptide detergent in accordance with the present invention. The scaffold peptide of LPD-16 has the following chemical structure:

wherein A is alanine, 0 is ornithine, E is glutamate, K is lysine, and Y is tyrosine, CH3CONH- is the acetylated amino terminal group of the peptide, and -CONH2 is the carboxamide end of the peptide chain. A single tyrosine is included to allow spectrophotometric detection of the peptide at 280 nm.

LPD-16 is synthesized on a solid support resin using a combination of Boc and Fmoc chemistries. The synthesis proceeds from the C-terminus of the peptide to the N-terminus, with all the main chain peptide synthesis couplings based on Fmoc chemistry. The resin tert-butoxycarbonyl-Alanine-methylbenzhydrylamine (Boc-Ala-MBHA) is chosen so as to produce a peptide carboxamide upon cleavage from the resin. The resin is first prepared by removal of the Boc protecting group with 50% trifluoroacetic acid (TFA), generating the free α-amino acid amine of the alanine. Sequential addition of the following 24 amino acids proceeds with the coupling of the appropriate Fmoc-protected amino acid: N-α-Fmoc-L-alanine (Fmoc-Ala), N-α-Fmoc-L-glutamamic acid α-benzyl ester (Fmoc-Glu(Obz)), N-α-Fmoc-N-α-2-chloro-benzyloxycarbonyl-L-lysine (Fmoc-Lys(2ClZ)), N-α-Fmoc-N-α-tertbutoxycarbonyl-L-ornithine (Fmoc-Orn(Boc)), or N-α-Fmoc-O-2-bromo-benzyloxycarbonyl-L-tyrosine (Fmoc-Tyr(2BrZ)) with the coupling reagent O-(7-azabenzotriazol-1-yl)-1,1,3,3-tetramethyluroniumhexafluorophosphate (HATU). Upon completion of the coupling reaction, the Fmoc protecting group is removed with 20% piperidine in preparation for the next amino acid coupling. Following the addition of the last amino acid and the removal of the Fmoc group, the amine terminus of the chain is acetylated with acetic anhydride. Next, the Boc protecting groups of the ornithine side chains are removed with 50% TFA in preparation for the coupling with the fatty acid. Two equivalents of hexadecanoic acid are coupled to the peptide with HATU. The final step involves the cleavage of the peptide from the resin and the deprotection of the glutamate, lysine, and tyrosine side chains with trifluoromethanesulfonic acid (TFMSA).

The lipopeptide is precipitated in ether, and washed four times in ether. The white pellet is dissolved in water, lyophilized, and redissolved in water. The peptide is purified by gel filtration chromatography in ammonium carbonate buffer, lyophilized, and redissolved in water. The lipopeptide is then purified by reverse-phase HPLC on a Waters PrepPak DeltaPak Cartridge (WAT038509, C4, 15 μm particle size, 300 Å, pore size, 25 mm×100 mm) at a flow rate of 20 mLs/min on a Perseptive Biosystems BioCAD HPLC workstation. The elution gradient is as follows: 2 minutes at 10% solution B/90% solution A, 2 minutes with a gradient from 10% to 40% buffer B, 40 minutes with a gradient from 40% to 80% buffer B, 2 minutes with a gradient from 80% to 90% buffer B. Solution A is 20 mM HCl in HPLC-grade water, and solution B is 20 mM HCl in acetonitrile. Eluted fractions are collected and analyzed by Matrix-Assisted Laser-Desorption Mass Spectrometry-Time-of-Flight mass spectrometry, and fractions containing the desired product are pooled and lyophilized to give the final, purifed product.

Lipopeptide detergents with pairs of aliphatic hydrocarbon tails of length 10, 12, 14, 16, 18, 20, 22, 24, and 28 carbons (LPD-10, LPD-12, LPD-14, LPD-16, LPD-18, LPD-20, LPD-22, LPD-24, and LPD-28) based on the peptide scaffold CH3CONH-AOAEAAEKAAKYAAEME-KAAKAOA-CONH2 have been designed and synthesized by coupling the peptide scaffold to decanoic acid, dodecanoic acid, tetradecanoic acid, hexadecanoic acid, octadecanoic acid, eicosanoic acid, docosanoic acid, tetracosanoic acid, and octacosanoic acid respectively. The LPDs with chain lengths from 10 to 16 carbons are soluble in water to over 10 mM, and the LPDs with chain lengths from 18 to 24 carbons are soluble to over 1 mM. LPD-28 is poorly soluble in water. Computer-assisted molecular modelling suggests that the alkyl chains longer than 16 carbons can cross past each other in LPD-16 through LPD24. As a control, a reference molecule known as C-0 is made with the same peptide scaffold, but without the coupled lipids. The C-0 peptide does not have detergent properties. Every batch of peptide is analyzed by MS to confirm the synthesis.

Example 2

Effectiveness of Lipopeptides in Stabililizing Solubilized Membrane Proteins

The membrane protein bacteriorhodopsin was purifed from *Halobacterium salinarium* (gift of J. Lanyi, University of California, Riverside) as follows. The bacteria were grown in 5 ml Standard Growth Medium (4.28 M sodium chloride, 81.1 mM magnesium sulfate heptahydrate, 10.2 mM sodium citrate, 26.8 mM potassium chloride, 10 g/L bacteriological peptone (Oxoid), 1.36 µM calcium chloride, 27.5 µM zinc sulfate heptahydrate, 12 µM manganese sulfate, 12 µM ferrous ammonium sulfate hexahydrate, 3.36 µM cupric sulfate pentahydrate, pH 7.0) with 1 mg/mL novobiocin with shaking for 5 days at 40° C. 3 mL of this culture were used to innoculate 300 mL standard growth medium with 1 mg/mL novobiocin, and the culture was grown for another three days at 40° C. with shaking. 16 mL of this culture was used to inoculate 800 mL of Standard Growth Media without novobiocin, and grown for 10 days at 40° C. with shaking. The cells were harvested by centrifugation at 16000×g for 10 minutes, and then resuspend in 100 mL 4 M NaCl, 0.5 mg/L DNaseI. The solution was then dialyzed with 12–14 kDa molecular weight cutoff (MWCO) membrane (Spectrum Laboratories Inc.) overnight at 4° C. against 12 L 0.1 M NaCl. Membranes were collected by centrifugation of the dialyzed solution at 100,000×g for 60 minutes. The membranes were washed 3 times in 0.1 M NaCl by repeatedly homogenizing the membrane pellet in 0.1 M NaCl with a Teflon pestle and centrifuging at 100, 000×g for 60 minutes. Purple membranes were isolated by overlaying 12.5 mL of the membrane suspension on a 40%/60% (10 mL/7.5 mL) sucrose gradient and centrifuging at 75,000×g overnight at 4° C. The purple membranes were removed from the sucrose density gradient and stored at −80° C.

The purple membranes were thawed and diluted 1:20 (v:v) in 0.1 M NaCl and spun at 100,000×g for 60 minutes at 4° C. The purple membranes were homogenized in 25 mM sodium phosphate, pH 6.9 with 1.5% OG (Anatrace, Maumee, Ohio) and mixed for 36 hours in the dark. After adjusting the pH to 5.5 with 0.1 N HCl, the solution was spun at 200,000×g for 45 minutes to obtain the soluble bacterioprhodopsin (BR) in the supernatant. The protein was concentrated to 5 mg/mL by ultrafiltration with an Amicon PM 10 membrane. BR was further purified from this solution by chromatography on a Superdex 75 gel filtration column in 25 mM sodium phosphate, pH 5.5, 1.2% (w/v) OG, at a flow rate of 1 mL/min.

OG is a standard detergent for the purification and crystallization of bacteriorhodopsin (G. F. Schertler et al., J. Mol. Biol 234, 156–164 (1993); Landau and Rosenbusch, *Proc Natl Acad Sci USA*, 93, 14532–5 (1996). To exchange the OG for a lipopeptide detergent, the appropriate LPD was added to 300 µL of a 0.5 mg/mL solution of BR in 25 mM NaPO4, 1.2% OG, pH 5.5 in a 5000 MWCO Biomax ultrafiltration concentrator. The solution was centrifuged at 10,000×g for 5 minutes, reducing the volume of the retentate to approximately 50 µl. The retentate was then diluted by the addition of approximately 250 µl of 50 mM NaPO4, 150 mM NaCl, pH 7.4, and the concentration/dilution cycle was repeated five times. The concentration of OG in the sample was monitored by a colormetric assay for carbohydrates as described by Dubois et al., *Anal. Chem.* 28. 350–356 (1956). Each concentration/dilution cycle reduced the OG concentration in the retentate by approximately 65%. Typically, the initial concentration of OG in the purified BR sample was approximately 50 mM, which is roughly twice the critical micelle concentration for this detergent. After three cycles, the concentration of OG was reduced to less than 5 mM, which is near the limit of sensitivity of the OG assay. After five concentration/dilution cycles, there was no detectable OG in the retentate by the OG assay. The estimated concentration of OG in the final sample was approximately 0.5 mM, or approximately 50 times less than the critical micelle concentration of OG. The recovery of BR and the LPD in the retentate was over 90% after five cycles.

The detergent exchanged samples were stored in the dark at room temperature, and at 1 day, 4 days, 7 days, 14 days 21 and 32 days storage, the samples were centrifuged at 100, 000×g for 45 minutes and the absorption spectrum of the supernatants were were recorded on a Pharmacia Ultraspec 200 spectrophotometer from 200 to 700 nm. Solubilized, properly folded, native bacteriorhodopsin remains in the supernatant and has an absorbance maximum at 550 nm. A control sample of BR was treated in the same way, except that OG was included in the dilution buffer for each of the 5 rounds of concentration/dilution. The spectra from a representative experiment with OG is shown in FIG. 2A, and spectra from a sample with LPD-16 is shown in FIG. 2B. The sample in OG lost the characteristic spectum for native bacteriorhodopsin within a few days, while the sample in LPD-16 remained virtually unchanged after 32 days.

FIG. 2C shows the result of a similar experiment in which the concentration of LPD-16 was varied from 0.25 mM to 2.5 mM in the final solution. All concentrations were effective at preserving the BR in a native state.

FIG. 2D shows a similar experiment but with different added lipopeptide detergents (LPD-12, LPD-14, LPD-16, LPD-18 and LPD-20), all at a final concentration of 0.5 mM. All were effective in preserving the BR in a native, soluble state. No protein was recovered in control samples without the additon of LPD prior to the five concentration/dilution steps (FIGS. 2C and 2D), confirming that the BR is insoluble in the absense of added detergent. The C-0 control peptide was not effective at maintaining BR in solution under these conditions (FIG. 2D), and demonstrates that the presence of the acyl chains on the peptide is essential for the effectiveness of the lipopeptide detergents.

Example 3

Interaction of Lipopeptide Detergents with Phospholipid Membranes

Phosphatidyl choline (PC) vesicles (liposomes) were prepared by extrusion through 0.1 nm pore membranes (Avestin, Ottawa), at 1 mM concentration in 10 mM N-[2-hydroxyethyl]piperazine-N'-[4-butanesulfonic acid (HEPES), 200 mM NaCl, pH 7.2, and diluted to 0.1 mM phospholipid in the same buffer. Dodecyl maltoside (DDM), C-0 peptide, or lipopeptide detergent in the same buffer were added to the indicated concentrations and the solutions were stored at room temperature for 24 hours. The hydrodynamic radius (Rh) and polydispersity of the solutions were measured on a DynaPro-800 dynamic light scattering device (Protein Solutions Inc., Charlottesville, Va.). Estimates on the error on the Rh values were taken as the polydispersity, as recommended by the manfacturer. Samples of DDM, C-0 peptide and LPD in the absence of PC liposomes were also analyzed.

The results of this experiment are illustrated in FIG. 3. The histogram demonstrates that the lipopeptide detergents LPD-12, LPD-14 and LPD-16 interact with phospholipid membrane vesicles, dissolving them into micelles. The control C-0 peptide had no measureable effect on these vesicles. The control sample with DDM confirms that the traditional detergent can also effect a transition. The initial liposomes have an Rh value of approximately 3240 nm, and the micelles have an Rh of 2.54.5 nm. The final concentration of DDM, peptide or lipopeptide in the samples were as follows: DDM with PC liposomes, 0.8 mM; DDM without liposomes, 1.0 mM; C-0 with PC liposomes, 2.0 mM; C-0 without liposomes, 2.2 mM; LPD-12 with PC liposomes, 1.25 mM; LPD-12 without liposomes, 1 mM; LPD-14 with PC liposomes, 1.5 mM; LPD-14 without liposomes, 0.9 mM; LPD-16 with PC liposomes, 1 mM; LPD-16 without liposomes, 0.9 mM. The exact Rh values did not depend strongly on the exact concentration of the added DDM or lipopeptide, as long as it was above the critical threshold value to effect the transition from liposomes to micelles in the samples with 0.1 mM PC.

The disclosures of all of the literature references and any patents referred to herein are incorporated herein by reference.

While the invention has been described with particular reference to certain embodiments thereof, it will be understood that those of ordinary skill in the art within the scope and spirit of the following claims may make changes and modifications.

In the claims, the word "comprising" means "including the following elements (in the body), but not excluding others"; the phrase "consisting of" means "excluding more than traces of other than the recited ingredients"; and the phrase "consisting essentially of" means "excluding unspecified ingredients which materially affect the basic characteristics of the composition".

I claim:

1. A lipopeptide detergent comprising a peptide moiety having the amino acid sequence AOAEAAEKAAKYAAE-AAEKAAKAOA (SEQ ID NO: 1) and comprising a first end and a second end, wherein said first end is covalently linked to a first aliphatic hydrocarbon moiety and said second end is covalently linked to a second aliphatic hydrocarbon moiety, said aliphatic moieties being linked such that they associate with a hydrophobic region of the peptide moiety.

2. The lipopeptide detergent as defined in claim 1, wherein said peptide comprises hydrophobic and hydrophilic regions.

3. The lipopeptide detergent as defined in claim 1, wherein said peptide comprises 15–35 amino acids.

4. The lipopeptide detergent as defined in claim 3, wherein said peptide comprises about 25 amino acids.

5. The lipopeptide detergent as defined in claim 1, wherein the length of said peptide is approximately equal to the width of a phospholipid bilayer.

6. The lipopeptide detergent as defined in claim 5, wherein the length of said peptide is in the range of about 3.5–4.0 nm.

7. The lipopeptide detergent as defined in claim 6, wherein the length of said peptide is about 3.7 nm.

8. The lipopeptide detergent as defined in claim 1, wherein the termini of said peptide are protected.

9. The lipopeptide detergent as defined in claim 8, wherein the N-terminus of said peptide is acetylated and the C-terminus of said peptide is amidated.

10. The lipopeptide detergent as defined in claim 1, wherein said aliphatic hydrocarbon moieties each comprise from about 8–24 carbon atoms.

11. The lipopeptide detergent as defined in claim 1, wherein said detergent is comprised of a peptide scaffold CH3CONH-AOAEAAEKAAKYAAEAAEKAAKAOA (SEQ ID NO: 1)-CONH2 coupled at each end to an aliphatic fatty acid selected from the group consisting of decanoic acid, dodecanoic acid, tetradecanoic acid, hexadecanoic acid, octadecanoic acid, eicosanoic acid, docosanoic acid, tetracosanoic acid, and octacosanoic acid.

12. The lipopeptide detergent as defined in claim 1, wherein each of said aliphatic hydrocarbon moieties is an aliphatic hydrocarbon tail having a length of from 10 to 28 carbon atoms.

13. The lipopeptide detergent as defined in claim 12, wherein each of said aliphatic hydrocarbon moieties is an aliphatic hydrocarbon tail having a length of 16 carbon atoms.

14. The lipopeptide detergent as defined in claim 12, wherein each of said aliphatic hydrocarbon moieties is an aliphatic hydrocarbon tail having a length of 12 carbon atoms.

15. A lipopeptide detergent as defined in claim 1, wherein said aliphatic hydrocarbon moieties are covalently linked to the peptide moiety at the ornithine residues of the peptide moiety.

16. A composition comprising membrane proteins stabilized by a lipopeptide detergent as defined in claim 1.

17. A composition comprising a biological membrane treated with a lipopeptide detergent as defined in claim 1.

* * * * *

SEQUENCE LISTING

```
<160> NUMBER OF SEQ ID NOS: 1

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence:synthetic
      lipopeptide
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (25)
<223> OTHER INFORMATION: AMIDATION
<220> FEATURE:
<221> NAME/KEY: MOD_RES
<222> LOCATION: (2,24)
<223> OTHER INFORMATION: X represents "ornithine"

<400> SEQUENCE: 1

Ala Xaa Ala Glu Ala Ala Glu Lys Ala Ala Lys Tyr Ala Ala Glu Ala
 1               5                  10                  15

Ala Glu Lys Ala Ala Lys Ala Xaa Ala
            20                  25
```